United States Patent [19]

Bucalo

[11] 4,005,699
[45] Feb. 1, 1977

[54] METHODS AND APPARATUS FOR USE IN MAGNETIC TREATMENT OF THE BODY

[76] Inventor: Louis Bucalo, 155 Roberts St., Holbrook, N.Y. 11741

[22] Filed: Oct. 9, 1974

[21] Appl. No.: 513,295

[52] U.S. Cl. .................................. 128/1.3; 3/36; 128/260
[51] Int. Cl.[2] ........................................ A61M 5/00
[58] Field of Search ........... 128/1 R, 1.3, 1.4, 213, 128/79, 260, 325, 21, DIG. 25, 5; 3/36; 222/95, 107, 193, 209, 212, 213, 214, 215, 544

[56] References Cited

UNITED STATES PATENTS

| | | | |
|---|---|---|---|
| 2,939,673 | 6/1960 | Rosholt | 128/1.3 |
| 3,419,008 | 12/1968 | Plishner | 128/1 R |
| 3,659,600 | 5/1972 | Merrill | 128/260 |
| 3,760,805 | 9/1973 | Higuchi | 128/213 |
| 3,794,020 | 2/1974 | Bagby | 128/79 |
| 3,794,041 | 2/1974 | Frei et al. | 128/1.3 |
| 3,853,122 | 12/1974 | Strauch et al. | 128/79 |
| 3,865,108 | 2/1975 | Hartop | 128/260 |

FOREIGN PATENTS OR APPLICATIONS

| | | | |
|---|---|---|---|
| 1,174,814 | 12/1969 | United Kingdom | 128/DIG. 25 |

OTHER PUBLICATIONS

Roth, "Journal of the American Medical Association," vol. 208, No. 5, p. 781, 5/5/69.

Primary Examiner—William E. Kamm
Attorney, Agent, or Firm—Steinberg & Blake

[57] ABSTRACT

Methods and devices for purposes such as magnetically treating tissue in a living being. There is injected into the tissue a viscous substance having a plurality of x-ray opaque bodies suspended therein to serve as a matrix for tissue growth. For the purpose of external magnetic control, the particles are magnetizable.

8 Claims, 5 Drawing Figures

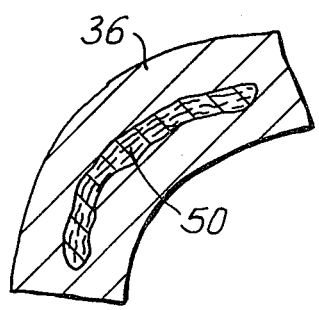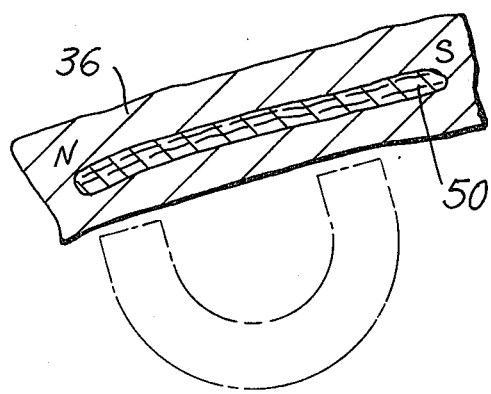

METHODS AND APPARATUS FOR USE IN MAGNETIC TREATMENT OF THE BODY

BACKGROUND OF THE INVENTION

The present invention relates to methods, materials, and devices to be used in providing for living beings magnetic treatments for influencing tissue.

As is well known, many individuals are troubled by the fact that parts of their bodies are not sufficiently attractive, symmetrical or physically functional. For example, patients are often disturbed by the feature damage resulting from accidents while male individuals are in many cases disturbed by the fact that the penis is too small. Also, in some cases individuals suffer from incontinence because of an incapability of controlling the urethra or anal canal. In addition, many male individuals suffer from an incapability of achieving satisfactory sexual intercourse, primarily because of an inability to achieve and maintain a satisfactory penile erection.

Many attempts have been made to solve problems of the above type. Thus, for example, it is known to introduce into the tissue quantities of a substance such as silicone, in order to enlarge tissue, but this solution to the problem of enlarging portions of body tissue is highly unsatisfactory since it results only in maintaining in the interior of the living being a quantity of a foreign substance which is uncontrollable in form and undesirable because of potential migration and difficulty in situating the substance at a desired location.

Procedures such as introducing a foreign substance into the body of a living being have been used in connection with relief of incontinence, but up to the present time no satisfactory solution has been provided for this problem, because of the difficulty of defining the configuration of the injected materials and the unstable nature of the implant form and shape.

In addition, in connection with rigid penile implants, while various procedures and devices have been used particularly in connection with simulating penile erection, up to the present time all of the known procedures have proved to be less than satisfactory because of radical alteration of natural conditions.

SUMMARY OF THE INVENTION

It is accordingly a primary object of the present invention to provide methods, materials, and devices for avoiding the above drawbacks.

In particular, it is an object of the present invention to provide methods and materials suitable for influencing body tissue.

Also, it is an object of the present invention to provide methods and materials for magnetic actuation of the injected materials without damaging surgery.

Furthermore, it is an object of the present invention to provide methods and devices for effectively achieving penile erection and artificially assisted sexual intercourse.

In accordance with the invention, for the purpose of influencing tissue, there is introduced into the tissue a viscous substance which has a plurality of bodies suspended therein and distributed therethrough. At least a portion of these bodies are magnetic, so that it is possible to achieve a magnetic influence on the body tissue.

BRIEF DESCRIPTION OF DRAWINGS

The invention is illustrated by way of example in the accompanying drawings which form part of this application and in which:

FIG. 4 is a schematic illustration of materials situated in tissue in an unmagnetized state; and FIG. 5 is a schematic illustration of materials situated in tissue in a magnetized state.

DESCRIPTION OF PREFERRED EMBODIMENTS

Figure 1:
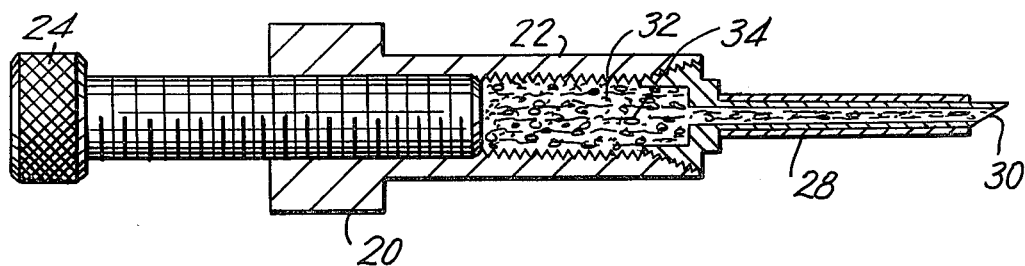
FIG. 1 is a fragmentary partly sectional schematic illustration of a syringe containing materials according to the invention which are introduced into tissue according to the method of the invention.

In connection with influencing tissue for purposes such as the enlargement of parts of the body in a living being, the method of the invention involves introducing into the tissue which is to be enlarged a viscous substance in which bodies are suspended while being distributed throughout the substance. The introduction of the substance with the bodies suspended therein is carried out, for example, by way of a screw type syringe 20 as schematically shown in FIG. 1. Thus, the syringe 20 has a hollow barrel 22 which receives the screw plunger 24. The outlet of the barrel 26 is connected to the needle 28 the tip 30 of which is introduced into the tissue at the part thereof which is to receive the materials (32 and 34) of the invention. These materials are shown in the barrel 22 in FIG. 1. Thus FIG. 1 shows a viscous substance 32 having the bodies 34 suspended therein and distributed therethrough.

In the preferred embodiment of the invention, the substance 32 is to be absorbed by the body and it may take the form of a vegetable oil or gelatin. The bodies 34 are preferably particles, but may include some elongated fibers as illustrated schematically in FIG. 1. Sufficient bodies 34 are suspended in the substance 32 so as to be distributed completely therethrough with the bodies 34 randomly engaging each other. The bodies 34 are made of materials which will be compatible with the body. Thus they may take the form of particles or fibers of gold, platinum, magnetic materials such as a platinum-cobalt alloy, gold plated magnetic materials, or the like, and it is also possible to use suitable absorbable materials or plastic materials for the bodies 34 combined with x-ray opaque materials.

According to a particular feature of the invention it is preferred to use for the substance 32 viscous hydrogenated vegetable oil, because in this case the time of absorption of the viscous substance may be controlled by the degree of hydrogenation, so that after the viscous substance 32 has been absorbed and replaced by tissue there remains in the living being an enlarged tissue portion composed of natural body tissue which itself has grown into the spaces between the bodies 34. Such methods and materials may effectively be used for cosmetic purposes such as changing facial features, or the like.

The use of varying degrees of hydrogenated cottonseed oil may be used for temporary implantation of solids. Thus, the viscous substance 32 may be very fluid unhydrogenated cottonseed oil which will be absorbed in a matter of days and the particles or fibers 34 composed of fully hydrogenated cottonseed oil which has the hardness of bone and which will require months for absorption. In this way varying rates of absorption and replacement by tissue are possible by varying the percentages of differentially hydrogenated components, as well as their size and shape. Such a method provides a temporary but effective result which may be repeated and is self-eliminating.

In addition, the varying rates of absorption may be utilized for the application of controllably releasing drugs and medications, such drugs and medications being absorbed at a rate controlled by the degree of hydrogenation of the injected vegetable oil, particles, as well as the size distributions of the absorbable particles rather than by chemical composition.

In addition, such methods and materials may be used in the penis for enlarging the same. For some individuals with permanent damage to the erectile systems, it is feasible to permanently enlarge the penis so that it can at any time penetrate into the vagina for effectively carrying out sexual intercourse. Thus, for this latter purpose a substance 32 such as hydrogenated vegetable oil having bodies 34 suspended therein can be introduced directly into the penile shaft in a manner according to which the substance is distributed along the penile shaft. This can be done by initially introducing the needle 30, and withdrawing the needle while simultaneously displacing the plunger 24 further into the barrel 22 so as to distribute the substance 32 and the bodies 34 therein in a desired manner along the penile shaft.

With the introduction of such materials into the penis, it may be permanently enlarged to an extent sufficient for reliably achieving penetration of the vagina whenever desired, and then as a further increase in the size of the penis takes place by natural means or artificial stimulation, the tissue itself will become further elongated because the injected implant will not damage the normal physiology as does surgically applied implants.

Furthermore, it is possible to vary the consistency of the mixture of fluid 32 and particles 34 by control of the viscosity of the fluid and the amount, material and shape of the particles 34. In particular, it is possible to vary the stiffness of the implant by the injection of magnetizable particles 50 as in FIG. 4 which particles 50 are injected in an unmagnetized condition into the penile shaft 36, for example, and subsequently magnetized by an external source as shown in phantom lines at the lower part of FIG. 5. Following magnetization of the particles, they will align and form a rigidized mass as illustrated. The condition may be reversed by demagnetization, thus returning to the condition illustrated schematically in FIG. 4.

Figure 2:
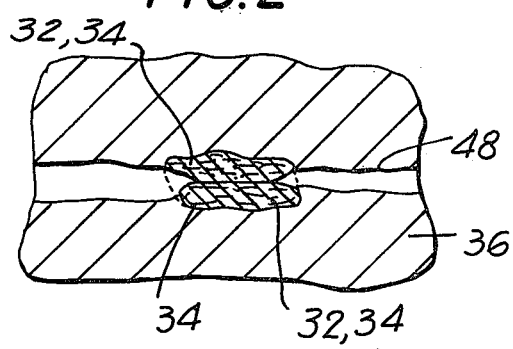
FIG. 2 is a schematic illustration of materials situated in tissue for the purpose of constricting a region of a body cavity.

Furthermore, as is well known, certain individuals suffer from incontinence in that they are unable to control discharges through the urethra or anal canal. For such individuals it is possible to introduce a ring of the substance 32 with the bodies 34 suspended therein around the passage 48 in the tissue 36 so as to relieve the condition of incontinence as shown in FIG. 2. In this case, the annular deposition of the substance 32 and the bodies 34 suspended therein around the urethra or anal canal is carried out in such a way that these tubular body passages are constricted somewhat by the introduced substance 32 and the bodies 34 suspended therein, in order to close the body passage 48 to prevent discharge therethrough except when normal urination or defecation pressure is provided to an extent sufficient to open the passage in opposition to the force of the deposited substance 32 and the bodies 34 suspended therein. Of course, in this case also, in connection with the alleviation of incontinence, it is preferred to use an absorbable substance 32 which will become replaced by living tissue which grows into the spaces between the fibers 34. Furthermore, it is preferred to use fibers which are opaque to x-ray such as fibers of gold, since such materials are most compatible and may be located by x-ray to verify their proper location. Also for these purposes (alleviation of incontinence, e.g.) injection of a mass of springy fibers is highly desirable.

Figure 3:
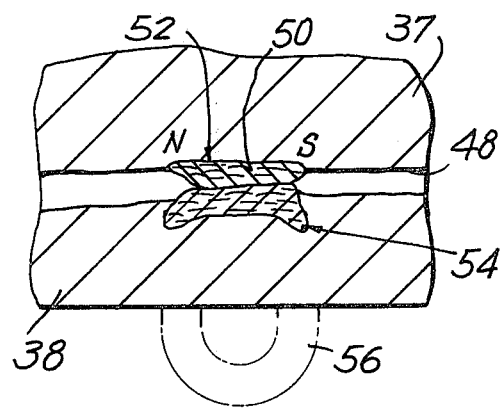
FIG. 3 is a schematic illustration of materials situated in tissue for the purpose of magnetically controlling the constriction of a body cavity.

As has been indicated above, it is desirable under some circumstances to inject a medium 32 containing magnetizable particles 50, and a further variation is shown in FIG. 3. Following injection in tissue 37 along the length of a body passage 48 on one side thereof the mass of particles may be subsequently magnetized to create a bar magnet assembly 52.

If subsequent to this procedure a mass 54 consisting of a substance 32 containing soft magnetic particles 50, (e.g. soft iron covered with gold) which are not magnetized is injected on the opposite side of the body passage 48 the constricting effect of the combined injections will be enhanced by the magnetic attraction of the parallel injected masses 52 and 54. Further it becomes possible to relieve the constriction of FIG. 3 by placing a more powerful opposing magnet 56 near the skin 38, thus creating magnetic attraction of the mass 54 and repelling mass 52. The resulting effect will cause the body passage to be relieved of constriction.

What is claimed is:

1. In a method of treating a living being, the step of injecting with a syringe, into tissue of the living being, an absorbable viscous substance, in which a plurality of solid bodies are suspended to an extent sufficient to be distributed throughout the viscous substance, in an amount sufficient to change the characteristics of the tissue receiving the injection, at least a portion of the bodies being non-absorbable, and at least a portion of the non-absorbable bodies being permanently magnetizable for maintaining the changed tissue characteristics independently of any outside source of magnetism.

2. In a method as recited in claim 1 and wherein following injection the bodies are magnetized from an external source to rigidize the masses of bodies when desired and demagnetized to relax the mass of bodies when desired.

3. In a method as recited in clam 2 and wherein the tissue of the living being is the penis and wherein said magnetized state simulates a penile erection.

4. In a method of treating a living being, the step of injecting with a syringe, into tissue of the living being, an absorbable viscous substance, in which a plurality of solid bodies are suspended to an extent sufficient to be distributed throughout the viscous substance, in an amount sufficient to change the characteristics of the tissue receiving the injection, at least a portion of the bodies being non-absorbable and at least a portion of the non-absorbable bodies being opaque to x-rays, the viscous substance with the bodies therein being distributed in tissue around a tubular passage through which discharge is required from time to time with the viscous substance and bodies therein at least partially constricting the tubular passage for alleviating incontinence, the bodies in the viscous substance being of magnetic material and wherein following initial injection of the substance containing said bodies the mass of said bodies is permanently magnetized from an external source thereby creating an initial permanent magnet mass composed of said bodies in the tissue near the tubular passage and wherein following said magnetization, a second injection of soft magnetic particles is performed along said tubular passage opposing said initial injection and wherein the magnetic forces acting between said initial permanent magnet and secondary soft magnetic injections by virtue of said initial permanent magnetic mass constrict the passage, thus alleviating incontinence.

5. In a method as recited in claim 4 and wherein the coonstriction caused by magnetic attraction of the said initially permanently magnetized mass and secondary magnetically responsive mass is controlled by a magnetic field applied external to the tissue.

6. In a method of treating a living being, the step of injecting with a syringe, into tissue of the living being, an absorbable viscous substance, in which a plurality of solid bodies are suspended to an extent sufficient to be distributed throughout the viscous substance, in an amount sufficient to change the characteristics of the tissue receiving the injection, at least a portion of the bodies being non-absorbable, and at least a portion of the non-absorbable bodies being permanently magnetizable, the viscous substance with the bodies therein being distributed around a portion of the circumference of a tubular body passage, through which flow is required, in at least two masses opposing each other and lying along said tubular passage and wherein said bodies are permanently magnetized in the same polarity to produce opposing magnetic forces in said masses thereby maintaining the passage in an open condition permitting a body fluid to flow.

7. In a method of treating a living being, the step of injecting with a syringe, into tissue of the living being, an absorbable viscous substance, in which a plurality of solid bodies are suspended to an extent sufficient to be distributed throughout the viscous substance, in an amount sufficient to change the characteristics of the tissue receiving the injection, at least a portion of the bodies being non-absorbable, and at least a portion of the non-absorbable bodies being permanently magnetizable and wherein in addition to magnetizable non-absorbable bodies the solid bodies include elastic bodies intermingled with the magnetizable bodies to be compressed thereby to a predetermined extent in accordance with the degree to which the magnetizable bodies are rendered magnetic and attract each other.

8. For use in the treatment of a living being, an absorbable viscous substance having suspended therein a plurality of solid bodies, and a plunger assembly, suitable for connection to an injection needle, enclosing said viscous substance and said solid bodies, said solid bodies including magnetizable bodies and elastic bodies intermingled with said magnetizable bodies.

* * * * *